United States Patent
Bolmsjö

[11] Patent Number: 6,119,045
[45] Date of Patent: Sep. 12, 2000

[54] DEVICE FOR MAINTAINING A PASSAGE FOR URINE THROUGH THE PROSTATE

[75] Inventor: Magnus Bolmsjö, Lund, Sweden

[73] Assignee: ProstaLund Operations AB, Lund, Sweden

[21] Appl. No.: 08/952,379

[22] PCT Filed: May 9, 1996

[86] PCT No.: PCT/SE96/00607

§ 371 Date: Nov. 12, 1997

§ 102(e) Date: Nov. 12, 1997

[87] PCT Pub. No.: WO96/35395

PCT Pub. Date: Nov. 14, 1996

[51] Int. Cl.$^7$ ................. A61F 2/00; A61N 1/04
[52] U.S. Cl. ................. 607/156; 607/101; 623/11
[58] Field of Search ................. 607/115, 116, 607/149, 154–156, 191–192, 96, 98, 99, 101; 623/11, 12

[56] References Cited

U.S. PATENT DOCUMENTS

| | | | |
|---|---|---|---|
| 4,503,569 | 3/1985 | Dotter . | |
| 4,893,623 | 1/1990 | Rosenbluth . | |
| 5,092,841 | 3/1992 | Spears | 604/96 |
| 5,391,196 | 2/1995 | Devonec | 607/96 |
| 5,562,641 | 10/1996 | Flomenblit et al. | 604/281 |
| 5,601,591 | 2/1997 | Edwards et al. | 606/198 |
| 5,662,712 | 9/1997 | Pathak et al. | 623/12 |
| 5,830,179 | 11/1998 | Mikus et al. | 604/49 |

FOREIGN PATENT DOCUMENTS

| | | |
|---|---|---|
| 0 449 472 A1 | 10/1991 | European Pat. Off. . |
| 2 661 604 | 11/1991 | France . |
| WO 91/17731 | 11/1991 | WIPO . |
| WO 93/13824 | 7/1993 | WIPO . |

*Primary Examiner*—Linda C. M. Dvorak
*Assistant Examiner*—Roy Gibson
*Attorney, Agent, or Firm*—Mathews, Collins, Shepherd & Gould, P.A.

[57] ABSTRACT

A device for maintaining a passage through the prostate gland (13) after treatment of a catheter (10) inserted through the urethra into the prostate gland, the catheter (10) being provided with means (11) for heating the prostate gland. A sleeve (12) is received over the catheter (10) so as to follow the catheter (10) during insertion into a desired position within the prostate gland, and the sleeve (12) is formed to remain in the desired position when the catheter is removed from the prostate gland, thereby maintaining a passage having a predetermined lower inner diameter through the prostate gland when tissue in the prostate gland swells.

7 Claims, 1 Drawing Sheet

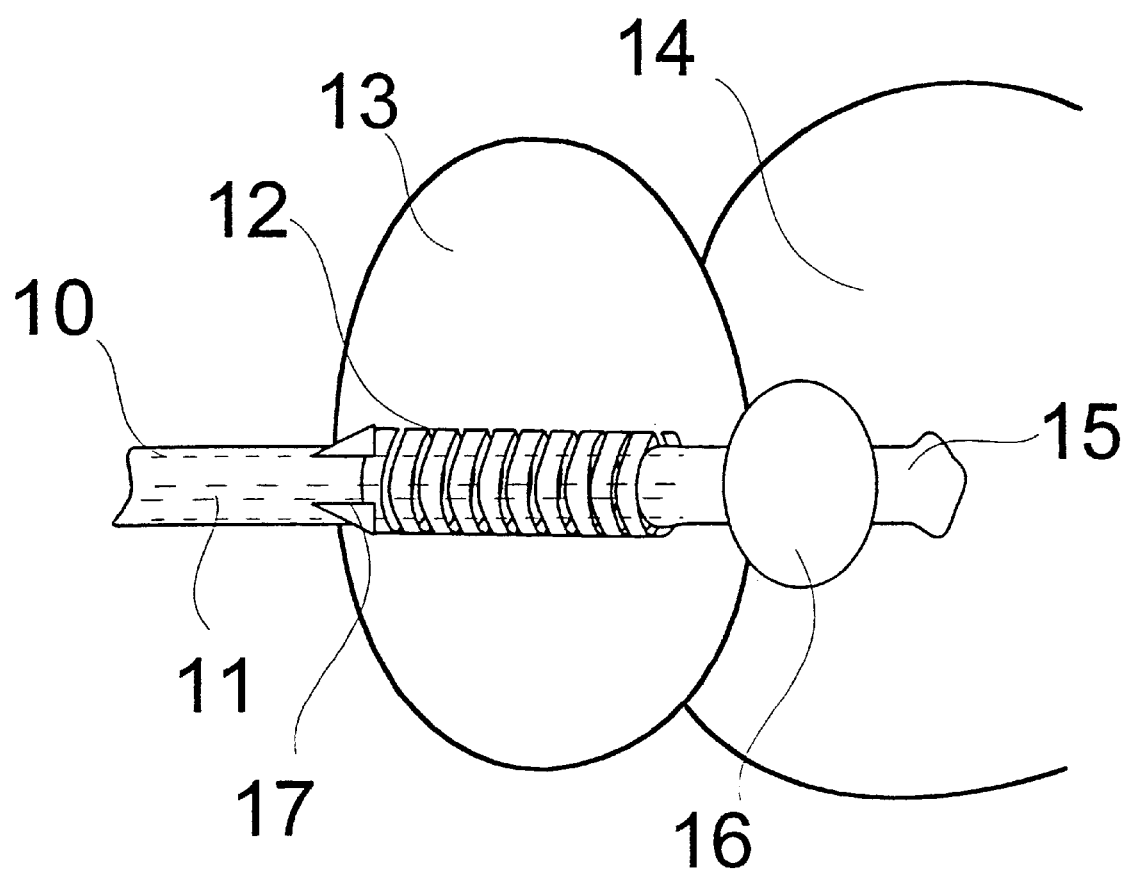

DEVICE FOR MAINTAINING A PASSAGE FOR URINE THROUGH THE PROSTATE

TECHNICAL FIELD

Prostate trouble, such as benign prostate hyperplasia (BPH) or chronic prostatism are found normally among men. In many cases the symptoms are experienced as very troublesome, and therefore numerous different forms of treatments have been developed. Several of these result in transitory trouble for some time after treatment.

The invention relates to a device for maintaining a passage for urine through the prostate gland as claimed in claim 1.

PRIOR ART

The purpose of microwave treatment and other heat treatments of the prostate gland is to accomplish an amount of dead tissue in the gland. The dead tissue is discharged in different ways, mainly through the urethra together with urine.

In connection with the treatment it is not unusual that an acute retention of the urinary tracts occurs to the patient. This is a result of a swelling of the heat treated prostate gland which closes the drain of urine. The effect can remain for a few months and is very troublesome to the patient.

To ensure a drainage of urine also during this period of time it is presently a normal step to insert a urine catheter during the time there is a swelling of the gland. Though there is a drain of urine according to this method the catheter as such is a problem to the patient.

DESCRIPTION OF THE INVENTION

An object of the present invention is to limit the risk of the troubles described above after treatment of the prostate gland. This object has been achieved according to characteristics of claim 1.

According to the invention a stent or sleeve or similar element is inserted in the prostate gland during the treatment. The sleeve is left after a completed treatment and remains in position during the time the tissue is swollen.

Preferably the sleeve is performed as a helical winding made of a material which after some time delay is desolved in contact with body tissue. An example of such a material is polyglycol acid (PGA). It is also possible to use a flexible tube.

DETAILED DESCRIPTION

According to the invention there is used a so called expanding stent or similar device, such as a flexible tube, which after completed treatment is attached along the prostatic urethra within the prostate gland in such a way that it prevents the swollen tissue from closing the drain of urine, instead maintaining an opening for a drain of urine.

The FIGURE shows an embodiment according to the invention using a stent 12 formed as a helical thread made of a suitable material. The stent 12 is arranged externally on a catheter 10 which during treatment is inserted through the urethra until a tip 15 has entered into the bladder 14. A balloon 16 following the catheter 10 into the bladder 14 is expanded through a duct in the catheter 10 to hold the catheter 10 in position in relation to the prostate gland 13. Within the catheter 10 there are provided means 11 for heating prostate tissue to such an extent that some tissue will be dead. Said means 11 preferably comprise a microwave antenna. To avoid too much dead tissue in the vicinity of the antenna cooling ducts can be provided in the catheter 10. Another way of providing a desired heating is to circulate heated liquid in a section of the catheter 10 positioned within the prostate gland, or in a separate container 18 of the catheter. It is also possible to provide separate heating means locally at the area of treatment and thereby to accomplish a local heating without any demand of cooling of surrounding tissue. The heating means may e.g. be some type of antenna which emits radio signals of a frequency in the interval 0,1–1000 MHz, or a volume of a liquid which is heated by a heating element.

The sleeve or the stent 12 is provided on the outside of the catheter 10. The stent 12 comprises a thread of a material that will be desolved in the tissue. The thread is winded in a helical winding. Preferably the inner diameter of the stent 12 is somewhat larger than the outer diameter of the catheter 10 to allow the stent 12 to slide comparatively freely on the outside of the catheter, and the outer diameter of the stent 12 is somewhat larger than the inner dimensions of the urethra through the prostate gland to fix the stent 12 to an appropriate extent within the prostate gland. The stent 12 can also be formed as a grid or a fabric.

During the treatment the stent 12 is passive and does not affect in any way the result of the treatment. After a completed treatment the balloon 16 is emptied. Then the catheter 10 is pulled out. To ensure that the stent 12 follows the catheter 10 into the desired location within the prostate gland wedgeshaped abutments 17 are provided on the outside of the catheter 10. In the shown simple embodiment it is the chosen dimensions of the stent and catheter that prevent the stent from following the catheter out from the prostate gland.

It is also possible to accomplish the same function with a flexible tube having a balloon-formed outer section which can be inflated and accomplish a mechanic contact with the prostate gland to accomplish the desired holding in position. It is also possible to hold the tube in other ways. However, the tube should be removable so as to be removed when it is less required. Normally, the requirement is smaller within 1–3 months. If a tube is used instead of a stent it is appropriate to provide a tube with ducts for draining the prostate gland. In this way it will be possible for treated and rejected necrotized tissue to be passed off through the urine.

In both embodiments the axial extension of the tube of the stent should not exceed the length of the prostate gland because the external sphincter adjacent to the rear part of the prostate gland should not be functionally disordered.

In some cases it is appropriate to hold the stent 12 or the tube by means of a separate tool in an immediate connection to the completion of the treatment. If a non-absorbing tube is used the tube is removed manually as soon as the tissue no longer is swollen. In such an embodiment the tube can be provided with a thread which is available and which can be used to pull out the tube. It is also possible to catch the tube and then pull it out.

To improve the transfer of heat between the heating means 11 and the tissue that is treated it may be appropriate to connect said means 11 to some type of heat conveying expansion means. The expansion means may include bimetal or any similar means which by an expansion will reach a good contact to the tissue.

What is claimed is:

1. A device for maintaining a passage through a prostate gland said device comprising:
   a catheter adapted to be inserted through an urethra to a prostate gland;

heating means for providing heat treatment of tissue of the prostate gland for accomplishing dead tissue, said heating means being provided in the catheter; and a sleeve received over the catheter to follow the catheter during insertion of the catheter through the urethra into a desired position within the prostate gland, said sleeve being formed with an outer diameter that is larger than an inner diameter of the urethra to allow the sleeve to remain in said desired position during said heat treatment and when the catheter is removed from the prostate gland, thereby maintaining a passage having a predetermined lower inner diameter through the prostate gland when tissue within the prostate gland is swollen as a result of said heat treatment.

2. The device according to claim 1 wherein said sleeve is formed of a material which is absorbed in body tissue.

3. The device according to claim 1 wherein said sleeve comprises means for holding said desired position of said sleeve in the prostate gland which is controlled from outside the body.

4. The device according to claim 1 wherein said heating means comprises an antenna for emitting electromagnetic radiation.

5. The device according to claim 1 wherein said heating means comprises a liquid container connected to a heating element for heating liquid enclosed in said container.

6. The device according to claim 1 wherein said heating means is connected to an expansion means, said expansion means expanding when heated in the direction of surrounding tissue of the prostate gland so as to increase the transfer of heat to said surrounding tissue.

7. A device for maintaining a passage through a prostate gland said device comprising:

a catheter adapted to be inserted through an urethra to a prostate gland;

heating means for providing heat treatment of tissue of the prostate gland for accomplishing dead tissue, said heating means being provided in the catheter; and a sleeve received over the catheter to follow the catheter during insertion of the catheter through the urethra into a desired position within the prostate gland, said sleeve being formed with openings to allow passage of dead tissue after said heat treatment and being formed with an outer diameter that is larger than an inner diameter of the urethra to allow the stent to remain in said desired position during said heat treatment and when the catheter is removed from the prostate gland, thereby maintaining a passage having a predetermined lower inner diameter through the prostate gland when tissue within the prostate gland is swollen as a result of said heat treatment.

* * * * *